US007947067B2

(12) United States Patent
Tucek et al.

(10) Patent No.: US 7,947,067 B2
(45) Date of Patent: May 24, 2011

(54) SCANNING TREATMENT LASER WITH SWEEP BEAM SPOT AND UNIVERSAL CARRIAGE

(75) Inventors: Kevin Tucek, Mesa, AZ (US); Steven C. Shanks, Mesa, AZ (US); Lawrence Owens, Mesa, AZ (US)

(73) Assignee: Erchonia Corporation, McKinney, TX (US)

( * ) Notice: Subject to any disclaimer, the term of this patent is extended or adjusted under 35 U.S.C. 154(b) by 533 days.

(21) Appl. No.: 11/409,408

(22) Filed: Apr. 20, 2006

(65) Prior Publication Data
US 2006/0224218 A1 Oct. 5, 2006

(51) Int. Cl.
*A61N 5/06* (2006.01)
(52) U.S. Cl. .................. 607/89; 606/2; 606/9; 606/13
(58) Field of Classification Search ... 606/9; 607/88–94
See application file for complete search history.

(56) References Cited

U.S. PATENT DOCUMENTS

| | | | |
|---|---|---|---|
| 2,987,960 A | 6/1961 | Sheldon | |
| 3,023,662 A | 3/1962 | Hicks, Jr. | |
| 3,653,384 A * | 4/1972 | Swope | 606/18 |
| 3,774,162 A | 11/1973 | Flaherty | |
| 3,966,319 A | 6/1976 | Lang | |
| 4,001,840 A | 1/1977 | Becker et al. | |
| 4,176,925 A | 12/1979 | Kocher et al. | |
| 4,729,372 A * | 3/1988 | L'Esperance, Jr. | 606/5 |
| 4,733,660 A * | 3/1988 | Itzkan | 606/9 |
| 4,767,930 A * | 8/1988 | Stieber et al. | 250/396 ML |
| 4,965,672 A | 10/1990 | Duke | |
| 4,984,892 A | 1/1991 | Hoffmann | |
| 5,095,386 A * | 3/1992 | Scheibengraber | 359/668 |
| 5,151,815 A | 9/1992 | Balliet | |
| 5,152,759 A * | 10/1992 | Parel et al. | 606/5 |
| 5,252,816 A | 10/1993 | Onimaru et al. | |
| 5,268,554 A | 12/1993 | Ream | |
| 5,284,477 A * | 2/1994 | Hanna et al. | 606/5 |
| 5,336,217 A | 8/1994 | Buys et al. | |
| 5,413,555 A * | 5/1995 | McMahan | 606/4 |

(Continued)

FOREIGN PATENT DOCUMENTS
DE 19725877 A1 12/1998
(Continued)

OTHER PUBLICATIONS

Canadian Intellectual Property Office, Requisition by the Examiner in Accordance with Subsection 30(2) of the Patent Rules, Jul. 14, 2010, Canada.

(Continued)

*Primary Examiner* — Henry M Johnson, III
*Assistant Examiner* — Lynsey Crandall
(74) *Attorney, Agent, or Firm* — Etherton Law Group, LLC; Annmarie W. Whitley; Sandra L. Etherton

(57) ABSTRACT

This invention is a scanning laser device with a universal carriage that holds any type of optical element. The carriage rotates about an axis that is substantially co-axial to the incident laser beam, thereby causing the laser energy passing through the optical element to sweep through a 360° circle. The preferred embodiment uses a rod lens as the optical element, resulting in a large circular beam spot. The device may utilize laser sources of various wavelengths and pulse frequencies, and multiple devices may be combined to scan an even larger area.

15 Claims, 8 Drawing Sheets

U.S. PATENT DOCUMENTS

| | | | |
|---|---|---|---|
| 5,422,471 A | 6/1995 | Plesko | |
| 5,461,473 A * | 10/1995 | Pratt et al. | 356/141.3 |
| 5,537,214 A | 7/1996 | Aiba et al. | |
| 5,653,706 A | 8/1997 | Zavislan et al. | |
| 5,743,902 A | 4/1998 | Trost | |
| 5,860,967 A | 1/1999 | Zavislan et al. | |
| 5,879,376 A | 3/1999 | Miller | |
| 5,968,033 A * | 10/1999 | Fuller et al. | 606/9 |
| 5,971,978 A | 10/1999 | Mukai | |
| 6,013,096 A * | 1/2000 | Tucek | 607/89 |
| 6,149,643 A * | 11/2000 | Herekar et al. | 606/5 |
| 6,168,590 B1 | 1/2001 | Neev | |
| 6,203,539 B1 * | 3/2001 | Shimmick et al. | 606/5 |
| 6,208,673 B1 * | 3/2001 | Miyake | 372/22 |
| 6,267,779 B1 * | 7/2001 | Gerdes | 607/89 |
| 6,273,884 B1 | 8/2001 | Altshuler et al. | |
| 6,312,451 B1 | 11/2001 | Streeter | |
| 6,328,733 B1 | 12/2001 | Trost | |
| 6,335,824 B1 * | 1/2002 | Overbeck | 359/368 |
| 6,358,272 B1 | 3/2002 | Wilden | |
| 6,383,177 B1 | 5/2002 | Balle-Petersen et al. | |
| 6,497,719 B2 | 12/2002 | Pearl | |
| 6,626,834 B2 | 9/2003 | Dunne et al. | |
| 6,641,578 B2 | 11/2003 | Mukai | |
| 6,666,878 B2 | 12/2003 | Carlgren | |
| 6,746,473 B2 | 6/2004 | Shanks | |
| 6,900,916 B2 | 5/2005 | Okazaki et al. | |
| 7,027,381 B1 * | 4/2006 | Nagasaka et al. | 369/275.1 |
| 7,101,365 B1 * | 9/2006 | Sharon | 606/9 |
| 2001/0053907 A1 | 12/2001 | Ota | |
| 2002/0104834 A1 | 8/2002 | Mangiarino | |
| 2002/0123781 A1 | 9/2002 | Shanks | |
| 2002/0138071 A1 | 9/2002 | Angeley et al. | |
| 2002/0138119 A1 | 9/2002 | Angeley et al. | |
| 2002/0154396 A1 * | 10/2002 | Overbeck | 359/368 |
| 2003/0189711 A1 | 10/2003 | Orr | |
| 2003/0218720 A1 | 11/2003 | Morita | |
| 2004/0030368 A1 | 2/2004 | Kemeny et al. | |
| 2004/0106856 A1 | 6/2004 | Kimura | |
| 2004/0123472 A1 * | 7/2004 | Wu | 33/286 |
| 2004/0199224 A1 * | 10/2004 | Shimmick et al. | 607/89 |
| 2004/0212863 A1 | 10/2004 | Schanz et al. | |
| 2005/0033388 A1 | 2/2005 | Brugger et al. | |
| 2006/0070251 A1 * | 4/2006 | Wu | 33/286 |

FOREIGN PATENT DOCUMENTS

| | | |
|---|---|---|
| DE | 19945087 A1 | 3/2001 |
| EP | 0130950 A2 | 9/1985 |
| SE | 510410 | 5/1999 |
| WO | WO 92/03187 A | 3/1992 |
| WO | WO 93/21993 A | 11/1993 |
| WO | WO 97/16126 A | 5/1997 |

OTHER PUBLICATIONS

State Intellectual Property Office, P.R. China, First Office Action, Jun. 4, 2010, Peoples Republic of China.

Korean Intellectual Property Office, Notice of Request for Submission of Argument, Oct. 15, 2010, Korea.

European Patent Office, Communication pursuant to Article 94(3) EPC, Feb. 16, 2009, Netherlands.

Response to First Office Action of State Intellectual Property Office, P.R. China, Sep. 30, 2010, China.

International Searching Authority, European Patent Office, International Search Report and Written Opinion, Jan. 28, 2008, Netherlands.

Israel Intellectual Property Office, Official Notification, Oct. 26, 2010, Israel.

Response to Communication pursuant to Article 94(3) EPC dated Feb. 16, 2009, Jun. 8, 2009, United Kingdom.

* cited by examiner

SCANNING TREATMENT LASER WITH SWEEP BEAM SPOT AND UNIVERSAL CARRIAGE

CROSS-REFERENCE TO RELATED APPLICATIONS

This application claims the benefit of U.S. patent application Ser. No. 10/772,738 filed Feb. 4, 2004, and U.S. patent application Ser. No. 10/976,581 filed Oct. 29, 2004, both of which claim the benefit of U.S. patent application Ser. No. 09/932,907 filed Aug. 20, 2001, now U.S. Pat. No. 6,746,473, which claims the benefit of U.S. Provisional Application No. 60/273,282 filed Mar. 2, 2001.

FIELD OF INVENTION

This invention relates generally to medical and chiropractic devices that employ lasers. More particularly, this invention relates to a treatment laser device that incorporates a scanning head that sweeps a beam spot.

BACKGROUND

Low level laser therapy (LLLT) utilizes low level laser energy in the treatment of a broad range of conditions. LLLT improves wound healing, reduces edema, and relieves pain of various etiologies, including successful application post-operatively to liposuction to reduce inflammation and pain. LLLT is also used during liposuction procedures to facilitate removal of fat by causing intracellular fat to be released into the interstice. It is also used in the treatment and repair of injured muscles and tendons, and for the stimulation of hair growth.

The LLLT treatment has an energy dose rate that causes no immediate detectable temperature rise of the treated tissue and no macroscopically visible changes in tissue structure. Consequently, the treated and surrounding tissue is not heated and is not damaged. There are a number of variables in laser therapy including the wavelength of the laser beam, the area impinged by the laser beam, laser energy, pulse frequency, treatment duration and tissue characteristics. The success of each therapy depends on the relationship and combination of these variables. For example, liposuction may be facilitated with one regimen utilizing a given wavelength and treatment duration, whereas pain may be treated with a regimen utilizing a different wavelength and treatment duration, and inflammation a third regimen. Specific devices are known in the art for each type of therapy.

Laser therapy has also been used as a depilatory to stop hair growth or to eliminate unwanted hair. These devices use relatively high-level laser energy, however, to thermally destroy offending hair follicles. U.S. Pat. No. 5,630,811 issued to Miller describes the evolution of lasers used to remove unwanted hair.

In contrast to the previously-accepted belief that lasers could be used only for hair removal because of the destructive result of the high-level laser energy, LLLT has been recognized recently as a method for hair restoration. One device designed to exploit the biostimulation effects of low level laser therapy to promote hair restoration is described in International Published Patent Application number WO02098509 assigned to Inca Asset Management S.A. of Geneva, Switzerland. This patent application describes a canopy or helmet, similar to the helmets used as hair dyers in hair dressing salons. The device is supported on a stand and positioned over the head of a patient. A helmet-like arrangement is placed inside the canopy so that it can rotate back and forth through about a quarter of a turn.

The invention requires alternate periods of laser stimulation and rest. This is achieved by forming several band shaped formations of laser diodes arranged in two lines on the inside of the helmet. As the helmet is oscillated the illumination from the laser diodes is swept across the scalp of the patient. The two lines are offset so that the scalp is fully illuminated as the helmet is rotated. A control panel on the front of the canopy is used to control the rotation of the helmet and the activation of the laser diodes. An alternate embodiment is described in which a large number of diodes are located on the inside of the helmet so that the entire scalp is illuminated without the need for a rotating canopy. The activation of the laser diodes is controlled to achieve the alternating periods of stimulation and rest required by the invention. A major drawback of this invention is the mechanical requirements to achieve a rotating helmet. Another drawback is the cost of using a large number of laser diodes.

Other methods of hair restoration are known, including hair follicle stimulation by light-emitting diode (LED), massage, and application of hormone-stimulating medicaments. For example, U.S. Pat. No. 6,666,878 issued to Carlgren discloses a helmet having rows of LEDs which create a band of light that moves repeatedly over the area of scalp to be treated. In addition to the discomfort of wearing a helmet repeatedly for extended periods, this device suffers the disadvantage of requiring many LED's to treat the scalp and limiting treatment areas to specific geometries, which can result in uneven hair growth.

Another device, described in U.S. Pat. No. 6,497,719 issued to Pearl et al., uses a laser in combination with a comb. The furrows create an unobstructed path for the laser beam to reach the scalp of the user. However, because each treatment is relatively long and many treatments are required, it is difficult to use a hand-held laser. The user's arm gets tired holding the laser for the required amount of time. This limits the precision and duration of the treatment.

Another hand-held laser is described in the inventor's U.S. Pat. No. 6,013,096. This patent describes a hand-held housing that houses a red semiconductor laser and optics to deliver the beam from the laser to the skin of a patient. A simple timing circuit is provided for controlling the length of time a laser beam is emitted from the wand. An optical arrangement causes the emitted light to form a line on the patient's skin, the shape of the light as it impinges the patient's skin referred to herein as the beam spot.

Reference may also be had to our U.S. Pat. No. 6,746,473 which describes a device that delivers two or more laser beams with different characteristics to treat a patient for multiple types of problems during a single treatment. The patent application describes a hand-held wand that houses a plurality of laser energy sources and optics to direct laser beams from the sources to a patient. Control electronics are provided to vary such parameters as the pulse repetition rate, known in the art as pulse frequency or pulse width. Optics are also provided to select the beam shape of the laser output, which in turn determines the beam spot.

It has been found that it would be advantageous to be able to apply a large beam spot on an area of a patient without significant hand motion by the therapist or without the use of many light sources. For example, with a large beam spot, a therapist can apply energy to nearly the entire area of a patient undergoing lipoplasty without having to manually move the laser back and forth over the patient for the required amount of time. It would also be desirable to apply energy to nearly the entire area of a patient undergoing hair treatments using a minimal number of lasers.

Therefore, an object of this invention is to provide a laser therapy device that incorporates a scanning head that sweeps a relatively large beam spot. It is a particular object of this invention to provide a therapeutic laser device with a sweep beam spot to provide low level laser therapy to treat injured muscles and tendons, post-operative inflammation and pain, and facilitate liposuction.

SUMMARY OF THE INVENTION

This invention is a scanning laser device with a universal carriage that holds any type of optical element. The carriage rotates about an axis that is substantially co-axial to the incident laser beam, thereby causing the laser energy passing through the optical element to sweep through a 360° circle. The preferred embodiment uses a rod lens as the optical element, resulting in a large circular beam spot. The device may utilize laser sources of various wavelengths and pulse frequencies, and multiple devices may be combined to scan an even larger area.

DETAILED DESCRIPTION OF THE INVENTION

Figure 1:
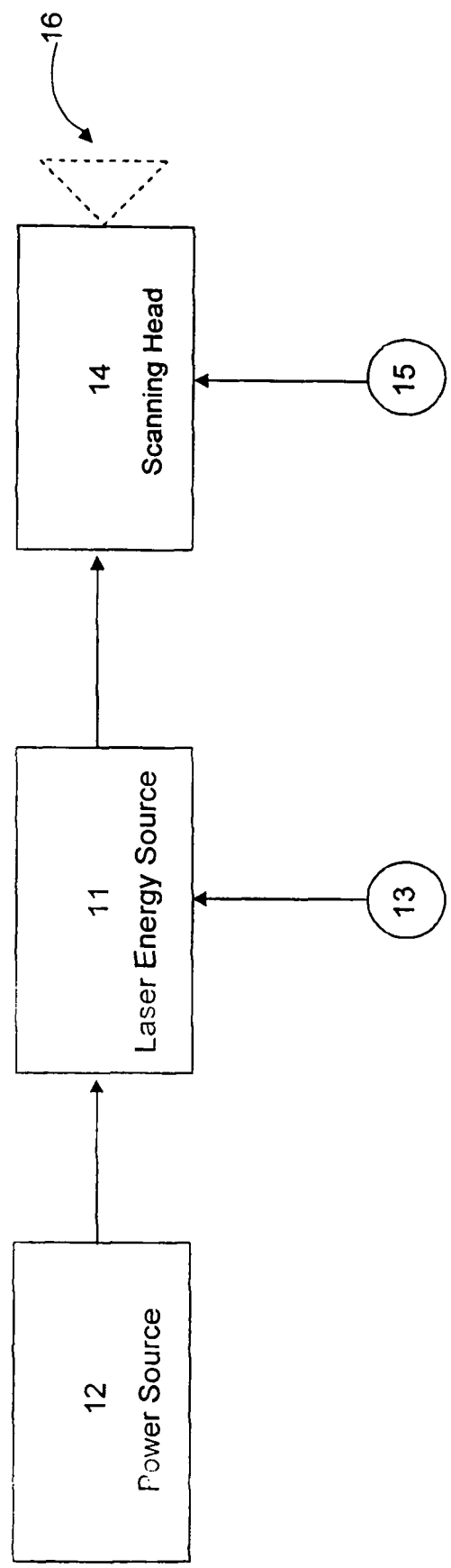
FIG. 1 is a schematic illustration of a preferred embodiment of the present invention.

FIG. 1 illustrates a schematic of a laser device that includes a power source 12, at least one laser energy source 11, a laser control 13, a scanning head 14, and a scanner control 15. In the preferred embodiment, the laser control 13 and scanner control 15 are incorporated into a control means 17. The power source preferably provides direct current, such as that provided by a battery, but may instead provide alternating current such as that provided by conventional building outlet power (e.g. 120V) that is then converted to direct current. The power supply 12 may be housed with the scanning head 14 or may be deployed separately with an electrical cable joining it thereto. Laser control 13 is connected to the laser energy source 11 and acts as on/off switch to control the period of time the laser light is generated and may also have other functions, such as controlling the pulse frequency. Other functions of the laser control 13, scanner control 15, and control means 17 are mentioned below.

Figure 2:
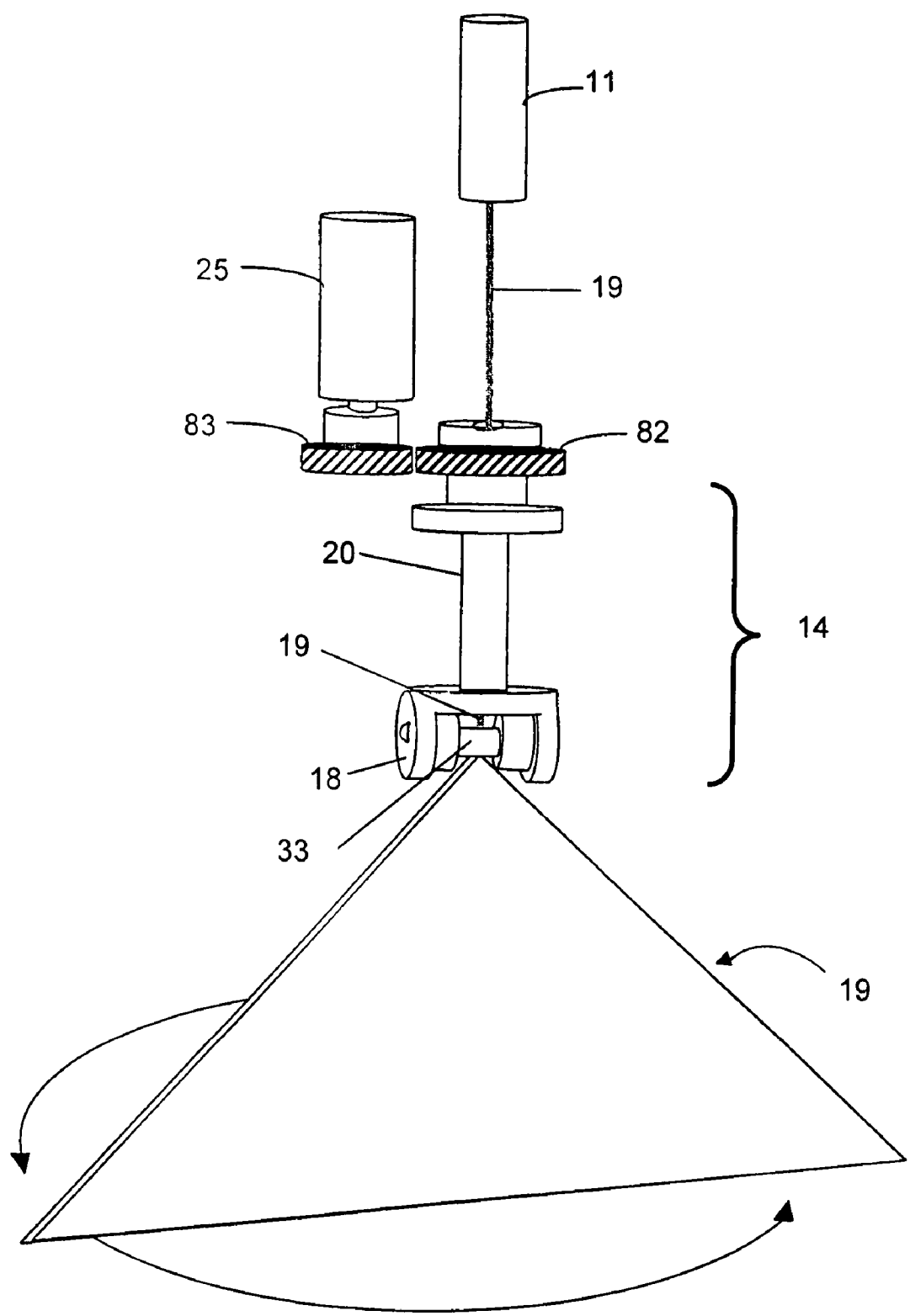
FIG. 2 is a perspective view of a preferred embodiment of the present invention.
Figure 3:
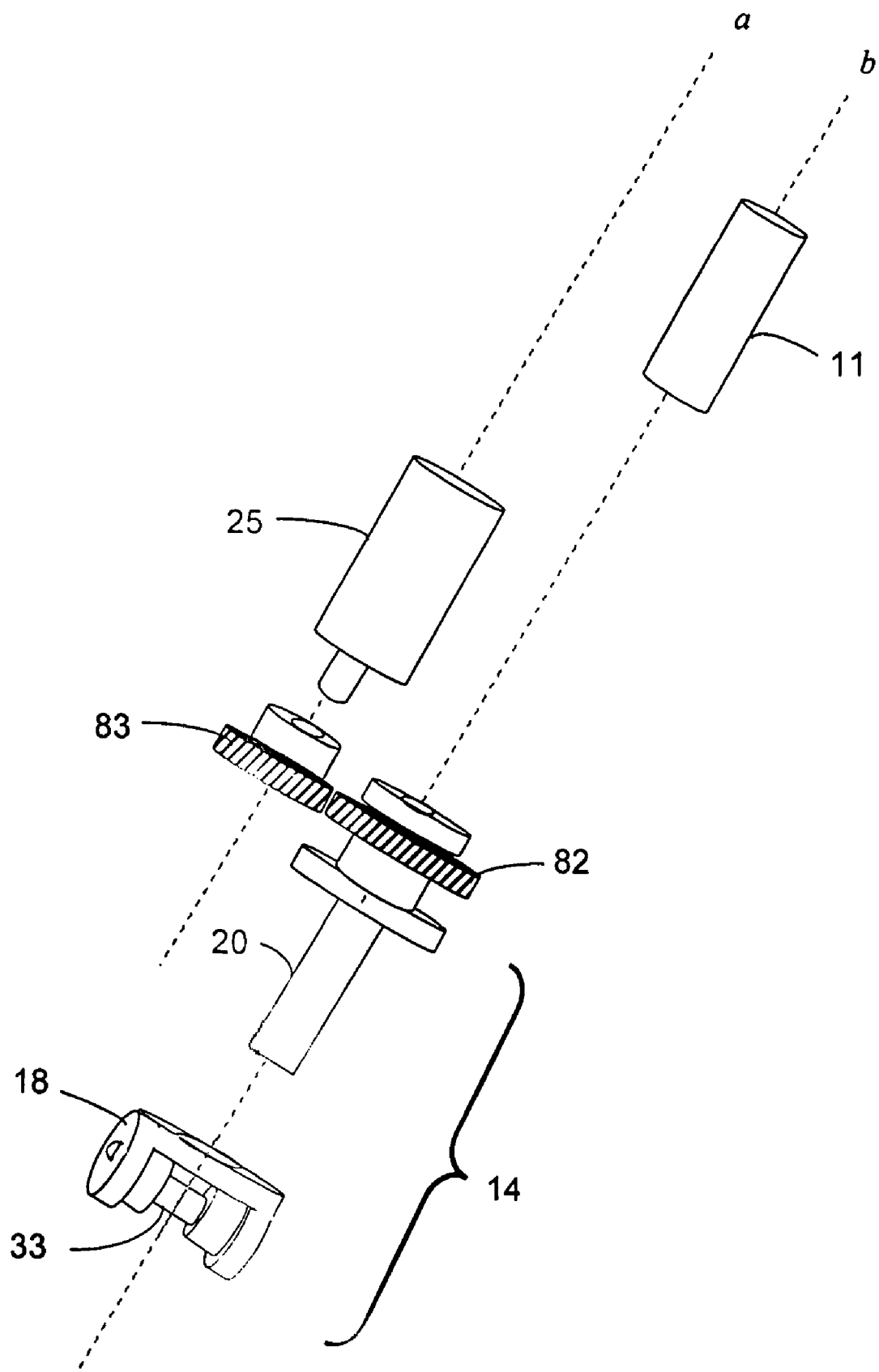
FIG. 3 is a perspective view of a scanning head of the preferred embodiment, exploded along axes a and b.
Figure 4:
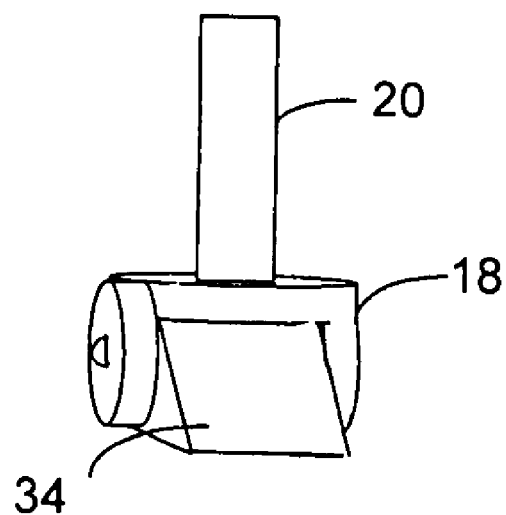
FIG. 4 is an the universal carriage holding a prism.
Figure 4A:
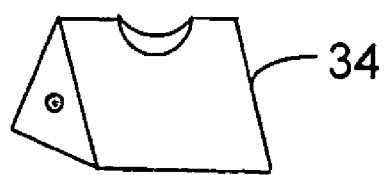
FIG. 4a is an exploded view of a prism holder and a prism.
Figure 4A:

A laser beam 19 emitted from the laser source 11 is directed to the scanning head 14. See FIG. 2. In the preferred embodiment, the scanning head comprises a hollow spindle 20 through which the laser beam 19 is conveyed. A rotatable carriage 18 holds an optical element upon which the laser beam 19 is incident. In the preferred embodiment, the laser beam 19, spindle 20 and carriage 18 are substantially coaxial. See FIG. 3.

Figure 5:
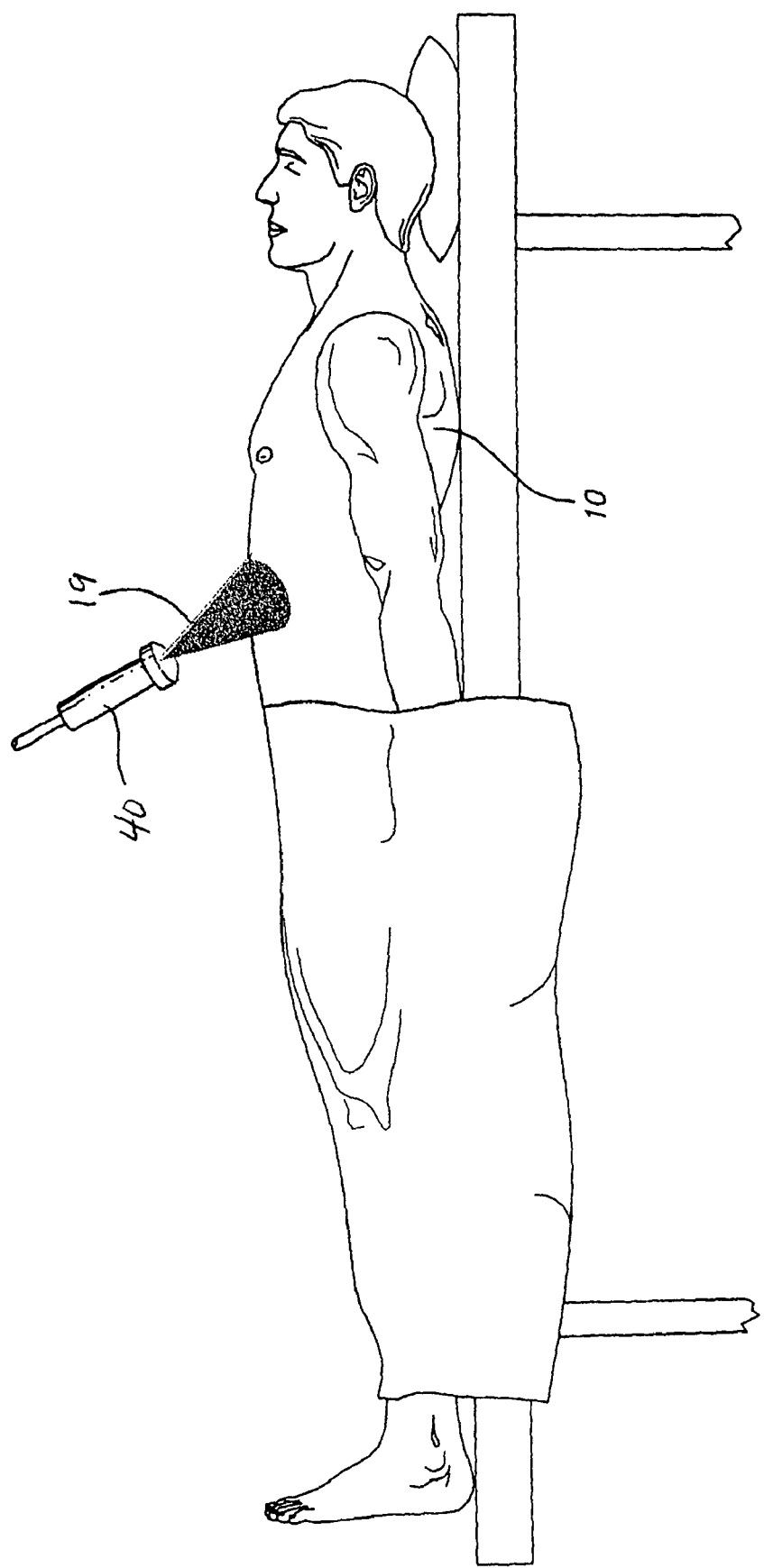
FIG. 5 illustrates a wand-mounted version of the preferred embodiment of the present invention producing a beam spot on a patient.

In the preferred embodiment, the optical element generates a line when laser light impinges on it. A rod lens 33 is preferred as the optical element, but a prism or other optical element or combination thereof may suffice. When the laser beam 19 strikes the optical element a line is generated. As the carriage 18 rotates, the line rotates, too, becoming, in essence, a rotating diameter of the apparent circular beam spot. If the carriage is rotated through 360°, the line also sweeps through a complete circle. With electronic or computerized control, the carriage is able to automatically rotate very quickly, causing the laser beam to appear to create a substantially circular beam spot on the patient's skin. See FIGS. 2 and 5. The shape, however, is actually the result of the scanning light diameter sweeping from location to location at a speed that makes the motion nearly imperceptible to the human eye. The longer the line, the larger the beam spot.

The carriage is rotated with a drive assembly. The drive assembly is preferably a main drive gear 82 which is mated with a minor drive gear 83. The minor drive gear is driven by a main drive motor 25. The carriage 18 rotates around the axis as the main drive gear 82 is turned. Thus, the laser beam from laser energy source 11 passes through the hollow spindle 20 and strikes an optical element which deflects the laser beam into a line that, in combination with the rotation, appears as a circular beam spot. The drive assembly may also be controlled by micromanipulators according to signals received from the scanner control 15, which is preferably incorporated into control means 17. Preferably the control means 17 is further comprised of various discrete circuits, as is known in the art. In a further form, the control means 17 is a microprocessor programmed to operate in various modes.

The laser light may be directed to the desired area on a patient using a hand-held wand. See FIG. 5. In the preferred embodiment, the wand is a housing comprising an elongated hollow tube defining an interior cavity. In the preferred embodiment the laser energy source 11 is mounted in the housing's interior cavity, although the laser energy source could be remotely located and the laser light conducted by fiber optics to the housing. The housing may take on any shape that enables the laser light to be directed as needed such as tubular, T-shaped, substantially spherical, or rectangular. The housing may contain the power supply (for example a battery) or the power supply may be remote with power supplied by an electrical cable. A scanning head may be contained wholly within each housing or attached separately to the end of each housing.

The scanner control 15 may also be programmed to move the scanning head 14 in a required manner to achieve any desired path of a treatment zone on the skin of a patient. Furthermore, the scanner control 15 can be programmed to direct the laser output into some regions more than others so that one region may have greater treatment than another region. The scan areas may overlap. This may be particularly useful for stand-alone apparatuses using the present invention, for example in a stand-alone laser device that provides low level laser therapy using one or more laser sources such as that described in the co-pending application Ser. No. 10/976,581, which is incorporated herein by reference and described below. The invention is not limited to any particular programmed operation mode, but by way of example the following modes of operation are available 1. The scanning head is programmed to move through a series of fixed regions and dwell for a pre-set period at each region. The regions may be input by a user to align with particular positions on the patient that require stimulation.
2. The wavelength is periodically changed by changing the operating laser diode during a repetitive scan. This allows stimulation of the patient at multiple wavelengths.
3. The focal position of the beam shaping optics is changed to generate smaller or larger spot sizes on the patient.
4. The laser power is varied.

Figure 6:
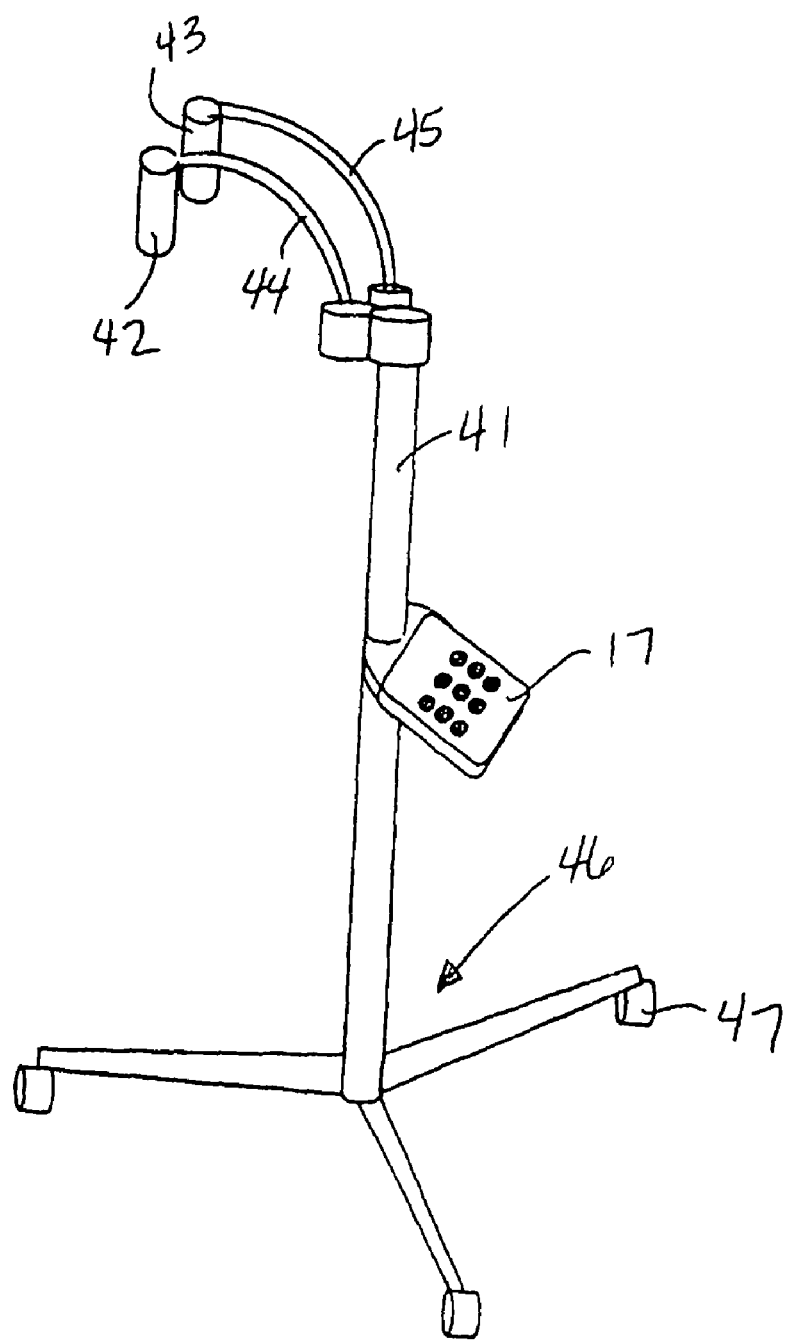
FIG. 6 illustrates a portable, floor-supported version of the preferred embodiment of the present invention.
Figure 7:
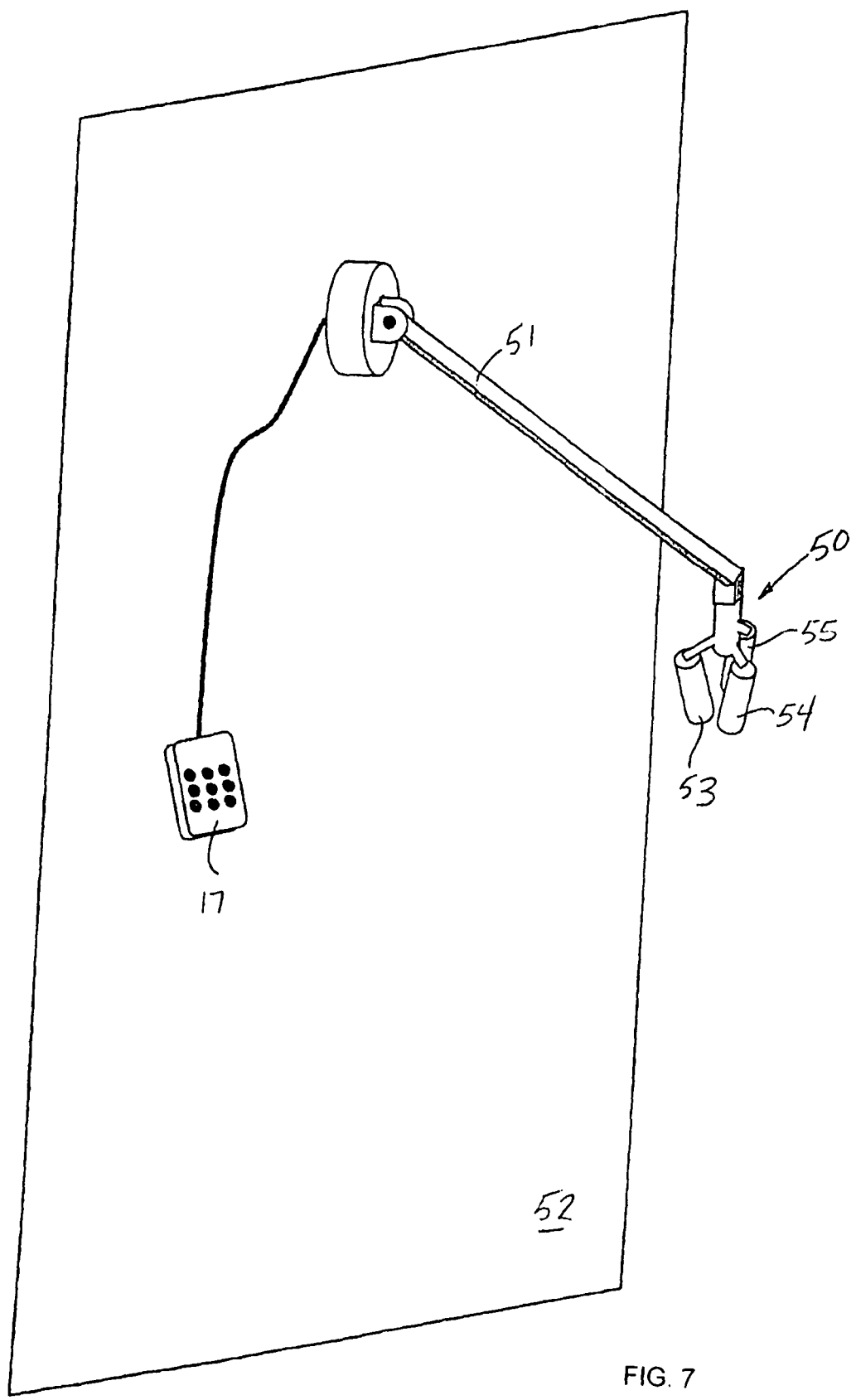
FIG. 7 illustrates a wall-mounted version of the preferred embodiment of the present invention.

Aw opposed to a hand-held device, he device may operate in a stand-alone configuration. For example, the present device may be supported by a support structure such as the wall or a portable stand that rests on the floor or table. This stand-alone arrangement enables a patient to be scanned by the laser beam without movement of the housing. FIG. 6 shows the portable, floor-mounted version of the present invention. Two-housings 42 and 43 are attached to arm 41 with connectors 44 and 45, respectively. The connectors may be rigid or, preferably, flexible, so that the housings can be moved to any desired position. The arm 41 may be articulated for additional control over the position of the lasers. The arm 41 is attached to a base 46 having wheels 47 such that the device can be moved to any desired position and then stay substantially stationary while treatment is occurring. This is particularly convenient for patients lying on a table or sitting in wheelchair. Control means 17 is in electrical connection with the housings and is shown in FIG. 6 mounted on the arm 41. The control, however, can be mounted elsewhere or can operate as a remote control using radio frequencies or other methods known in the art.

Figure 8:
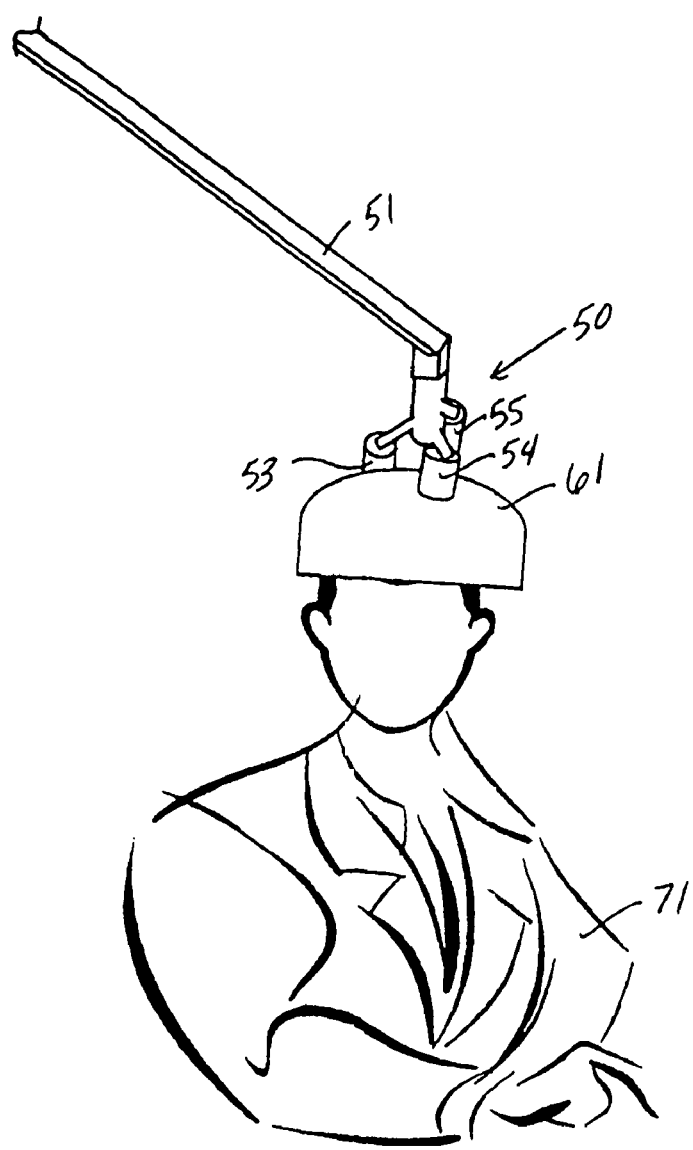
FIG. 8 illustrates a version of the present invention employing a shield.

FIG. 8 shows a three-housing assembly 50 attached to a wall-mounted arm 51. The arm 51 is affixed to the wall 52 in ways known in the art such that it can be moved to any desired position and then stay in substantially stationary while treatment is occurring. The arm may be articulated for additional control over the position of the lasers. Control means 17 is in electrical connection with the housings and is shown in FIG. 10 mounted on the wall. The control, however, can be mounted elsewhere or can operate as a remote control using radio frequencies or other methods known in the art. The assembly 50 is attached to the arm 51 in ways known in the art such that it can be moved to any desired position. Likewise, the housings 53, 54, 55 are attached to the assembly so that each can be moved to a desired position.

A shield may be employed to prevent the laser light from reflecting or deflecting to undesired locations. Se FIG. 8. The shield is attached where appropriate to block the radiation. For example, the shield 61 may be attached to the assembly, to one or more of the housings, or worn by the patient. FIG. 11 illustrates a shield 61 that blocks the laser light that may reflect or deflect off the patient's head. It is shaped like a canopy or helmet and preferably is attached to the assembly 50 such that the housings 53, 54, 55 protrude through the shield 61 to ensure that no laser light escapes the canopy. The shield may take on other shapes, as appropriate, depending on the area to be shielded. For example, the shield may take on a rectangular or hemi-cylindrical shape to shield a patient's upper torso.

FIG. 8 illustrates the application of low-level laser radiation for hair restoration. Patient 71 is balding and the laser assembly 50 is positioned above his head. The patient can remain comfortably seated or lying on a table throughout the treatment and no therapist intervention is required to treat the patient.

In the preferred embodiment, each housing 53, 54, 55 is directed by the control means 17 to deliver a desired scan pattern 73, 74, 75 respectively with a desired laser output across the patient's scalp. Due to the nature of the laser light, the patent can be treated through any existing hair, so it is unnecessary to touch the hair or scalp to clear a pathway for the laser.

Most low level laser treatments have proven to be effective at a single wavelength in the red region of the spectrum, between about 630 nm and about 670 nm. However, it has been shown that LLLT can be effective throughout the visible, near infrared and near ultraviolet regions. Laser diodes are currently available to cover only a limited part of the available spectrum, so other laser energy sources may be used. To obtain maximum benefit it may be desirable to stimulate the patient at two or more different wavelengths. Persons skilled in the art will be aware that various laser energy sources are known in the art for use in low-level laser therapy. They include Helium-Neon lasers having a 632 nm wavelength and semiconductor diode lasers with a broad range of wavelengths between 600-800 nm. The laser energy source in the preferred embodiment is a semiconductor laser diode that produces light in the red range of the visible spectrum, having a wavelength of about 635 nm. Other suitable wavelengths are used for other particular applications. The preferred embodiment is described as having a single laser energy source 11 but it will be appreciated that the invention may have two or more laser energy sources. These laser sources may be attached to each other in a laser assembly or individually attached to a support structure. While many LLLT regimen include ultraviolet or infrared laser light, it is advantageous to utilize at least one laser beam in the visible energy spectrum so that the operator can see the laser light as it impinges the patent's body and the area treated can be easily defined.

Different therapy regimens require diodes of different wattages. The preferred laser diodes use less than one watt of power each to simultaneously facilitate liposuction, treat post-operative inflammation and post-operative pain, as well as to restore hair. Diodes of various other wattages may also be employed to achieve the desired laser energy for the given regimen. It may be advantageous to provide a power source separate from the housing, and deliver the power to the housing by wire. An advantage of the present invention is that a larger treatment area can be achieved without the need for a higher power laser.

Laser control 13, preferably incorporated into control means 17, controls the duration of each pulse of laser light emitted and the pulse frequency. When there are no pulses, a continuous beam of laser light is generated. Pulse frequencies from 0 to 100,000 Hz or more may be employed to achieve the desired effect on the patient's tissue. The goal for LLLT regimen is to deliver laser energy to the target tissue utilizing a pulse width short enough to sufficiently energize the targeted tissue and avoid thermal damage to adjacent tissue.

While there has been illustrated and described what is at present considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment disclosed as the best mode contemplated for carrying out the invention, but that the invention will include all embodiments falling within the scope of the appended claims.

We claim:

1. A laser device comprising:
   a) at least one laser energy source for generating a laser beam; and b) a scanning head further comprising:
  i. a hollow spindle substantially coaxial with the laser beam and through which the laser beam is conveyed;
  ii. a refractive optical element through which the laser beam is conveyed to produce a linear first beam spot whose centerpoint is along the axis of the hollow spindle;
  iii. a rotatable carriage housing the optical element and through which the laser beam is conveyed and which, when rotated, creates an apparent solid circular second beam spot whose center is along the axis of the hollow spindle; and
  iv. means for continuously rotating the carriage through 360 degrees.

2. The device of claim 1 further comprising a drive assembly for rotating the carriage.

3. The device of claim 2 wherein the drive assembly further comprises:
  a) a main drive gear;
  b) a minor drive gear; and
  c) a motor that drives the main drive gear which cooperates with the minor drive gear to rotate the carriage.

4. The device of claim 1 wherein the optical element is a prism.

5. The device of claim 1 wherein the optical element is a rod lens.

6. The device of claim 1 further comprising a scanner control for controlling the movement of the optical element.

7. The device of claim 1 wherein at least one laser energy source is a semiconductor diode.

8. The device of claim 1 wherein the laser energy source generates a laser beam having a wavelength in the visible range.

9. The device of claim 1 wherein the laser energy source generates a laser beam having a wavelength in the red range.

10. The device of claim 1 further comprising a laser control for controlling a pulse frequency of the laser beam.

11. The device of claim 1 comprising at least two laser energy sources, at least one of said laser energy sources emitting a visible laser beam.

12. The device of claim 1 further comprising a hand-held wand in which the carriage is housed in a position to maintain operability of the device without the wand touching a patient's skin.

13. The device of claim 1 further comprising a stand-alone support structure in which the carriage is housed in a position to maintain operability of the device without the device touching a patient's skin.

14. The device of claim 1 wherein the first beam spot is a line.

15. The device of claim 14 wherein the second beam spot is a circle.

* * * * *